United States Patent [19]

Glamkowski et al.

[11] 3,997,539
[45] Dec. 14, 1976

[54] 3-(4-ACYLAMINOPIPERAZIN-1-YL ALKYL)INDOLES, PRECURSORS AND PROCESSES FOR THE PREPARATION THEREOF

[75] Inventors: Edward J. Glamkowski, Warren; Philip A. Reitano, Raritan, both of N.J.

[73] Assignee: American Hoechst Corporation, Bridgewater, N.J.

[22] Filed: May 31, 1974

[21] Appl. No.: 475,315

[52] U.S. Cl. .................. 260/268 BC; 424/250
[51] Int. Cl.² ............................. C07D 295/04
[58] Field of Search .............. 260/268 BC, 268 N

[56] References Cited
UNITED STATES PATENTS

| 2,663,706 | 12/1953 | Conroy | 260/268 N |
|---|---|---|---|
| 2,663,707 | 12/1953 | Conroy et al. | 260/268 N |
| 3,188,313 | 6/1965 | Archer | 260/268 BC |
| 3,297,689 | 1/1967 | Cusic et al. | 260/268 N |

Primary Examiner—Paul M. Coughlan, Jr.
Attorney, Agent, or Firm—Curtis, Morris & Safford

[57] ABSTRACT

New 3-(4-acylaminopiperazin-1-ylalkyl)indole compounds, and their immediate precursors possessing antihypertensive and tranquilizing properties, their physiologically acceptable salts and a process for the preparation thereof are described; said compounds are of the general formula:

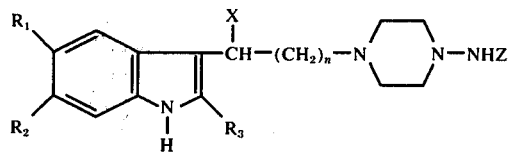

wherein X represents hydrogen or hydroxy, n can vary from 0-1, $R_1$ and $R_2$ each represents hydrogen or alkoxy of 1-2 carbon atoms; $R_3$ represents hydrogen or alkyl of 1-3 carbon atoms and Z represents hydrogen or

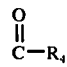

and $R_4$ is selected from a member of the group consisting of alkyl of 1-4 carbon atoms, benzhydryl, cycloalkyl of 6-10 carbon atoms; bridged cycloalkyl of 6-10 carbon atoms, phenyl, mono, di or tri substituted phenyl, and heterocyclic moieties such as pyridyl, furyl, pyrrolyl, thienyl, pyrazinyl.

32 Claims, 3 Drawing Figures

3-(4-ACYLAMINOPIPERAZIN-1-YL ALKYL)INDOLES, PRECURSORS AND PROCESSES FOR THE PREPARATION THEREOF

This invention relates to 3-(4-acylaminopiperazin-1-ylalkyl)indoles and immediate precursors, and their physiologically acceptable salts; these indoles, whether final products or precursors, possess antihypertensive and tranquilizing activity. A method for their preparation is within the scope of this invention. It is believed that the compounds of this invention have not heretofore been described.

BRIEF DESCRIPTION OF PRIOR ART

3-Indolylalkyl-amines are known and have been shown to possess important biological activity. Benzamidopiperidylethylindoles are reported to be potent antihypertensive agents [Archibald et al., J. Med. Chem., 14, 1054 (1971)], and 1-[(3-indole)alkyl]-4-arylpiperazines are reported to be active as central nervous system depressants [Wylie et al., J. Med. Phar. Chem., 5, 932 (1962)].

BRIEF DESCRIPTION OF THE INVENTION

The compounds of the invention are represented by the formula:

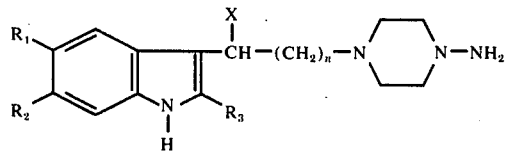

and the formula

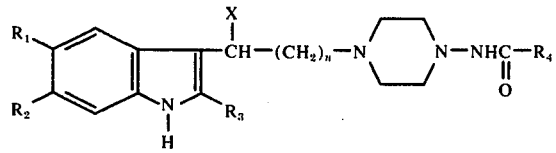

wherein X represents hydrogen or hydroxy, $n$ can vary from 0–1, $R_1$ and $R_2$ each represents hydrogen or alkoxy of 1–2 carbon atoms, $R_3$ represents hydrogen or alkyl of 1–3 carbon atoms; and $R_4$ represents alkyl of 1–4 carbon atoms, benzhydryl, cycloalkyl of 6–10 carbon atoms, bridged cycloalkyl of 6–10 carbon atoms with the bridging member having from 1–3 carbon atoms, phenyl, mono, di or tri substituted phenyl and heterocyclic moieties such as pyridyl, furyl, pyrroloyl, thienyl, pyrazinyl, preferably furyl or substituted furyl; and physiologically tolerable addition salts, i.e., acceptable addition salts of the above compounds are also within the scope of the invention. When $R_4$ represents a substituted phenyl, the substituents can be on any of the five available positions of the benzene ring and the substituents can be a halogen, straight or branched chain alkyl of 1–4 carbon atoms, alkoxy of 1–4 carbon atoms, trifluoromethyl, nitro, phenyl, sulfamyl, or hydroxy, when $R_4$ represents substituted furyl the substituents may be on the three available positions and may be halo, preferably bromo, or lower alkyl, preferably methyl; of the above indole compounds those where $n$ is 1 and X is hydrogen including where $R_1$ and $R_2$ each is hydrogen and $R_3$ is hydrogen and methyl are preferred; of this group, the substituents where $R_4$ is substituted or unsubstituted furyl and phenyl are the most preferred compounds. Next, as a group, the indole compounds where $n$ is 0 and X is hydrogen is a desirable group, the other substituents in this group being the same as for the above group.

DETAILED DESCRIPTION OF THE INVENTION

Figure 1:
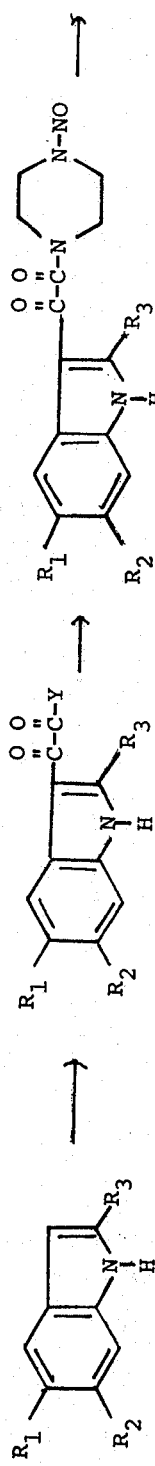

The compounds of the present invention are prepared by one of three multi-step sequence of reactions as described below and illustrated in the attached drawings, with the exceptions noted in the drawings, in which X, $n$, $R_1$, $R_2$, and $R_3$, and $R_4$ are as defined above. 3-[2-(4-acylaminopiperazin-1-yl)ethyl]indoles of the formula:

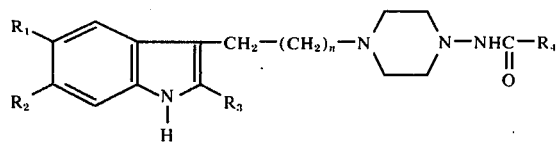

wherein $n$ is 1, are prepared by the following sequence designated as Method A and shown in FIG. 1. Starting with the substituted indoles known in the literature, the 3-(indolyl)glyoxalyl halides of formula I(a) are prepared by the method of Speeter et al., J. Am. Chem. Soc., 76, 6209 (1954).

The intermediates so prepared are reacted with N-nitrosopiperazine at a temperature between −10° to 100° C. to give the 3-1-(indol-3-ylglyoxyloyl)-4-nitrosopiperazines of formula II(a). This reaction may or may not be carried out in a solvent or mixture of solvents. An added inorganic base such as potassium carbonate, or an organic base such as triethylamine, may be used to bind the hydrogen halide liberated during the course of the reaction; and added base is optional because N-nitrosopiperazine itself can serve as the hydrogen ion acceptor.

Preferably, the reaction is carried out by adding the 3-(indolyl)glyoxalyl halide to a chloroform and water mixture containing the N-nitrosopiperazine and potassium carbonate while maintaining the temperature at 20°–25° C. over a span of from 1 minute to 60 minutes. This affords the crude product indole of formula II(a) in a nearly quantitative yield. With certain acid sensitive indoles such as when $R_1$ and $R_2$ represent methoxy and $R_3$ represents methyl, it may be advantageous to combine the first two steps of this method in one reaction vessel without isolating their sensitive intermediate of formula I(a). For example, a mixture of 5,6-dimethoxy-2-methylindole and potassium carbonate in chloroform is treated with oxalyl chloride at −5° C. and the resulting glyoxalyl chloride is reacted in situ with N-nitrosopiperazine to produce the intermediate of formula II(a).

Reduction of 3-(indolyl) glyoxamides of formula II(a) with an alkali metal hydride for a half hour to 24 hours, produces the 3-[2-(4-aminopiperazin-1-yl)ethyl]indoles of formula III(a). This reduction is carried out in an organic solvent which is inert under the conditions of the reaction, for example, in ether, tetrahydrofuran, or 1,2-dimethoxyethane and at a temperature ranging from −10° C. to the boiling point of the solvent.

In a preferred embodiment of the reaction, lithium aluminum hydride is used as the reducing agent and 1,2-dimethoxyethane is the solvent, and the mixture is refluxed to produce a nearly quantitative yield of a compound designated as III(a), i.e., one of the novel compounds herein.

Acylation of the 3-[2-(4-aminopiperazin-1-yl)ethyl]indoles with a reactive derivative of an acid of the general formula $R_4COOH$, wherein $R_4$ represents the groups defined above, for from 5 minutes to 24 hours, by methods known in the art, produces the 3-[2-(4-acylaminopiperazin-1-yl)ethyl]indole compounds of this invention. Preferably, an acid halide or acid anhydride is used in this acylation. When the above is 3-[2-(4-acylaminopiperazin-yl)ethyl]indole, wherein $R_4$ is

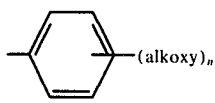

and $n$ is the integer 1, 2, or 3, these alkoxy groups can be dealkylated by methods known in the art to produce

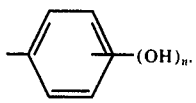

3-[1-Hydroxy-2-(4-acylaminopiperazin-1-yl)ethyl] indoles of the formula

Figure 2:
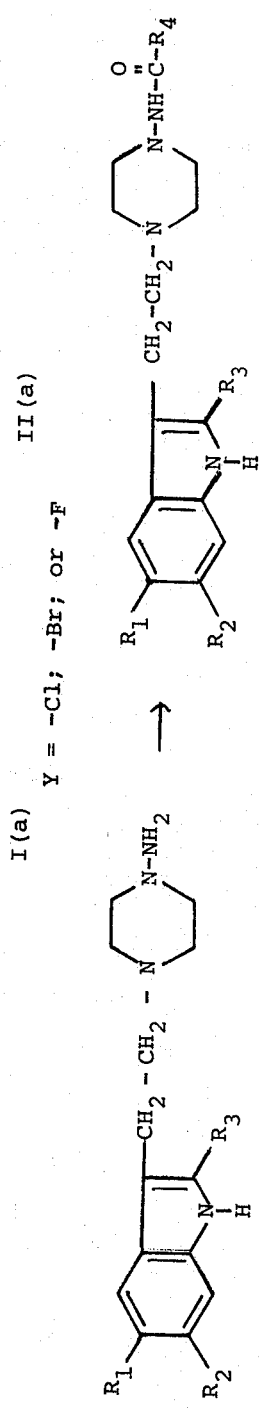

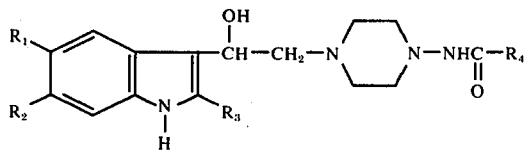

wherein $R_1$, $R_2$, $R_3$, and $R_4$ are as described above, are prepared by the following sequence designated as Method B and shown in FIG. 2. When the aforementioned reduction of glyoxamides of formula II(a) with an alkali metal hydride is carried out in a lower boiling inert solvent, either at reflux temperature or below, the reduction is incomplete and compounds of the 3-[1-hydroxy-2-(4-aminopiperazin-1-yl)ethyl]indoles of the formula III(b) are produced. These may be separated from any of the fully reduced intermediates of formula III(a), also produced in the reaction, by crystallization or other methods known in the art. One preferred system utilizes lithium aluminum hydride as the alkali metal hydride and tetrahydrofuran (b.p. 65°–67° C.) as the inert solvent.

Acylation as previously described in Method A takes place selectively at the amino group to yield the 3-[1-hydroxy-2-(4-acylaminopiperazin-1-yl)ethyl]indoles of formula IV(b) in FIG. 2, compounds of the invention herein.

Figure 3:
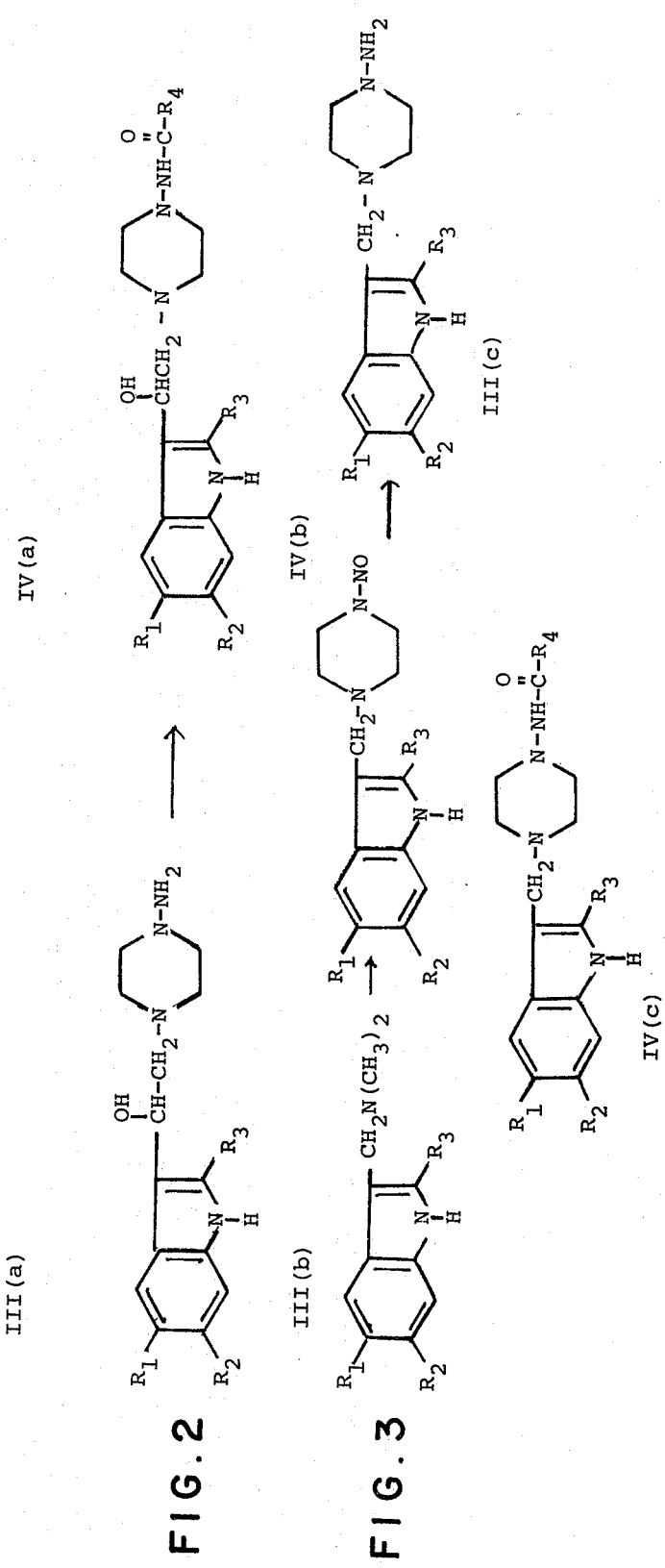

3-(4-Acylaminopiperazin-1-yl)methylindoles of the formula:

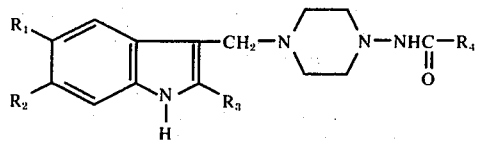

wherein $R_1$, $R_2$, $R_3$, and $R_4$ are as described above, are prepared by the following sequence designated as Method C and shown in FIG. 3. A 3-dimethylaminomethylindole is allowed to react with N-nitrosopiperazine in an inert solvent for 1–48 hours to produce the 3-(4-nitrosopiperazin-1-yl) methylindoles in high yields. A preferred embodiment utilizes toluene as the inert solvent at refluxing conditions for 1–2 days.

Reduction with an alkali metal hydride in an appropriate inert solvent produces the 3-(4-aminopiperazin-1-yl) methylindoles, compounds of this invention of the formula III(c) illustrated in FIG. 3. Preferably, this reduction is effected with lithium aluminum hydride in 1,2-dimethoxyethane by refluxing for from 0.5 hour-6 hours.

Acylation as previously described with respect to Method A also produces the 3-(4-acylaminopiperazin-1-yl) methylindole of formula IV(c) as illustrated in FIG. 3. These are also novel compounds.

Within the purview of this invention are the pharmaceutically acceptable, i.e., tolerable, acid addition salts of the 3-(4-amino and the 3-(4-acylaminopiperazin-1-yl) alkylindoles which are prepared according to well known procedures. Representative of such salts are those formed with mineral acids, such as the hydrochloride, hydrobromide, sulfate, phosphate and the like, and the organic acid salts, such as the maleate, oxalate, succinate, pamoate, p-toluenesulfonate, and the like.

The compounds of this invention are useful as antihypertensive agents due to their ability to depress blood pressure in mammals. Antihypertensive activity was measured in the spontaneous hypertensive rat by the indirect tail cuff method described in A. Schwartz, Ed., *Methods in Pharmacology*, Vol. I, page 135, Appleton-Century Crofts, New York, New York, 1971.

In a standard 3 day test, according to this procedure, systolic blood pressure readings were made at 0 time (control) on days 1 and 3. Dosing was orally at 100 mg/kg at 0 hour on days 1, 2 and 3 on groups of 6 animals per test. Activity was determined by comparison of the treated host's blood pressure values with the 0 time (control) blood pressure readings. A value of −15 mm Hg or more is considered significant.

The antihypertensive activity in this test of some of the compounds of the invention is illustrated in Table I.

TABLE I

| Compound of the General Formula | | | | | | Day 1 mm Hg | Day 3 mm Hg |
|---|---|---|---|---|---|---|---|
| $R_1 + R_2$ | $R_3$ | X | n | Z | $R_4$ | | |
| H | H | H | 1 | $\underset{O}{\overset{\|}{C}}-R_4$ |  | −24 | −56 |

TABLE I-continued

| Compound of the General Formula | | | | | | Day 1 mm Hg | Day 3 mm Hg |
|---|---|---|---|---|---|---|---|
| H | H | H | 1 | C—R₄ (C=O) | —⟨⟩—F | -56 | -57 |
| H | H | H | 1 | C—R₄ (C=O) | —⟨⟩ with OCH₃, OCH₃, OCH₃ | -63 | -70 |
| H | H | H | 1 | C—R₄ (C=O) | furan | -58 | -64 |
| H | H | H | 1 | C—R₄ (C=O) | norbornyl | -53 | -42 |
| H | H | H | 1 | C—R₄ (C=O) | —CH₃ | -32 | -40 |
| H | H | OH | 1 | C—R₄ (C=O) | —⟨⟩ | -30 | -33 |
| H | CH₃ | H | 1 | C—R₄ (C=O) | —⟨⟩ | -39 | -37 |
| H | H | H | 1 | C—R₄ (C=O) | —⟨⟩ with OCH₃, OCH₃ | -46 | -111 |
| H | H | H | 1 | H | — | -36 | -46 |
| H | CH₃ | H | 1 | H | — | -59 | -31 |

Z is an acyl moiety or hydrogen as indicated.

Compounds of the invention are also useful as tranquilizing agents because of their depressant effects on the central nervous system. These tranquilizing effects were measured according to the mouse observation procedure of S. Irwin, Psychopharmacologia, 9, 259 (1966). In this test, male mice (type COBS) were dosed orally with the drug and its effects on behavior and reflex depression, together with muscle relaxation, were determined by the degree of deviation from control scores. The overall result for 3 animals in each category for some compounds of this invention is expressed in terms of the minimum effective dose (MED) and is illustrated in Table II.

TABLE II

| Compound of the General Formula | | | | | | MED (mg/kg body weight) |
|---|---|---|---|---|---|---|
| $R_1 + R_2$ | $R_3$ | X | n | Z | $R_4$ | |
| H | H | H | 1 | C—R₄ (C=O) | —⟨⟩—C(CH₃)₃ | 75 |
| H | H | H | 1 | C—R₄ (C=O) | —⟨⟩—CF₃ | 75 |
| H | H | H | 1 | C—R₄ (C=O) | —⟨⟩ with OCH₃, OCH₃, OCH₃ | 37 |
| H | H | H | 1 | C—R₄ (C=O) | norbornyl | 40 |
| H | H | H | 1 | C—R₄ (C=O) | —CH₃ | 75 |
| H | CH₃ | H | 1 | C—R₄ (C=O) | —⟨⟩—F | 40 |
| CH₃O | CH₃ | H | 1 | C—R₄ (C=O) | —⟨⟩ | 75 |
| CH₃O | CH₃ | H | 1 | C—R₄ (C=O) | —⟨⟩—F | 75 |
| H | H | H | 1 | H | — | 40 |

Z is an acyl moiety or hydrogen as indicated.

Examples of the compounds of the invention are:
3-[2-(4-aminopiperazin-1-yl)ethyl]indole;
3-[2-(4-benzamidopiperazin-1-yl)ethyl]indole;
3-{2-[4-(3,4,5-trimethoxybenzamido)piperazin-1-yl]ethyl}indole;

3-[2-(4-p-fluorobenzamidopiperazin-1-yl)ethyl]indole;
3-[2-(4-t-butylbenzamidopiperazin-1-yl)ethyl]indole;
3-[2-(4-p-trifluoromethylbenzamidopiperazin-1-yl)ethyl]indole;
3-[1-hydroxy-2-(4-benzamidopiperazin-1-yl)ethyl]indole;
3-[2-(4-acetamidopiperazin-1-yl)ethyl]indole;
3-{2-[4-(2-furoylamidopiperazin-1-yl]ethyl}indole;
3-[2-(4-norbornanecarbonylamidopiperazin-1-yl)ethyl]indole;
3-[2-(4-benzamidopiperazin-1-yl)ethyl]-2-methylindole;
3-[2-(4-benzamidopiperazin-1-yl)ethyl]-5,6-dimethoxy-2-methylindole;
5,6-dimethoxy-3-[2-(4-p-fluorobenzamidopiperazin-1-yl)ethyl]-2-methylindole;
3-(4-benzamidopiperazin-1-yl)methylindole;
3-[2-(4-o-methoxybenzamidopiperazin-1-yl)ethyl]indole;
3-[2-(4-m-methylbenzamidopiperazin-1-yl)ethyl]indole;
3-[2-(4-biphenylcarbonylamidopiperazin-1-yl)ethyl]indole;
3-{2-[3,5-dimethoxybenzamido)piperazin-1-yl]ethyl}indole;
3-{2-[4-chloro-3-sulfamylbenzamidopiperazin-1-yl]ethyl}indole;
3-[2-(4-diphenylacetamidopiperazin-1-yl)ethyl]indole;
5,6-dimethoy-2-methyl-3-[2-(4-p-trifluoromethylbenzamidopiperazin-1-yl)ethyl]indole hydrochloride;
3-[2-(4-aminopiperazin-1-yl)ethyl]-5,6-dimethoxy-2-propylindole hydrochloride;
3-[2-(4-benzamidopiperazin-1-yl)ethyl]-5-ethoxy-2-ethyl-6-methoxy indole;
3-{2-[4-(5-bromo-2-furoylamidopiperazin-1-yl)]ethyl}indole;
3-{2-[4-(4-methyl-2-furoylamidopiperazin-1-yl)]ethyl}indole.

Effective quantities in the range from 0.1–100 mg/kg body weight of any of the pharmacologically active 3-(4-acylaminopiperazin-1-ylalkyl)indoles may be administered to a patient by any one of various methods, for example, orally as in capsules or tablets, parenterally in the form of sterile solutions or suspensions, and in some cases intraveneously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 0.1–100 milligrams of active compound.

The tablets, pills, capsules, troaches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, Shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For parenteral administration, the carrier or excipient may be a sterile, parenterally acceptable liquid; e.g., water or a parenterally acceptable oil, e.g., arachis oil contained in ampules.

As an illustration of the invention but not to limit it thereby a number of examples are to follow. These examples or the tables herein illustrate various facets of the invention.

EXAMPLE 1

3-[2-(4-Aminopiperazin-1-yl)ethyl]indole a. To a solution of 13.6 g (0.096 mol) of potassium carbonate in 60 ml. of water is added a solution of 8.06 g (0.070 mol) of N-nitrosopiperazine in 60 ml. of chloroform. The two phases are stirred vigorously while 12.4 g (0.060 mol) of indole-3-glyoxyl chloride is introduced in portions for 15 minutes while maintaining the reaction temperature at 20°–25° C. The resultant gummy mixture is stirred for an additional 2 hours and then 50 ml. of ethyl ether is added in portions. The gummy solid is thereby crystallized, stirred for an additional 15 minutes, and the crystalline product is filtered, washed with water, then with ethanol (2 × 25 ml.) and dried to produce crystals of 1-(indol-3-ylglyoxyloyl)-4-nitrosopiperazine. This material is recrystallized from DMF (dimethylformamide) and water to produce pure crystals having a m.p. 223°–225° C. Analysis: Calculated for $C_{14}H_{14}N_4O_3$:58.74% C; 4.93% H; 19.57% N Found: 58.77% C; 5.01% H; 19.66% N.

b. To a stirred mixture of 9.0 g of lithium aluminum hydride in 400 ml. of 1,2-dimethoxyethane is added 10.52 g (0.037 mol) of 1-(indol-3-ylglyoxyloyl)-4-nitrosopiperazine slowly to maintain reaction temperature below 35° C. After all the material is added, the mixture is refluxed for 14–16 hours. The reaction mixture is cooled to −5° C. and a solution of 50 ml. of water and 50 ml. of 1,2-dimethoxyethane is slowly added while maintaining the temperature below 15° C. Another 50 ml. of water is added, and the mixture is then filtered. The solvent is removed from the filtrate and the residual solid is recrystallized from benzene, producing the pure crystals of 3-[2-(4-aminopiperazin-1-yl)ethyl]indole, m.p. 115°–117° C. Analysis: Calculated for $C_{14}H_{20}N_4$:68.82% C; 8.25% H; 22.93% N Found:68.70% C; 8.17% H; 22.55% N.

EXAMPLE 2

3-[2-(4-Aminopiperazin-1-yl)ethyl]-2-methylindole a. To a solution of 41.4 g (0.30 mol) of potassium carbonate in 300 ml. of water is added a solution of 38.1 g (0.33 mol) of N-nitrosopiperazine in 300 ml. of chloroform. The two phases are stirred vigorously while 66.4 g (0.30 mol) of 2-methyl-indole-3-glyoxyl chloride is introduced in portions for 30 minutes. The resultant mixture is stirred for an additional 0.5 hour and then 300 ml. of ethyl ether is added in portions. The product is filtered, washed with water, then with ethanol and dried to afford crystals of 1-(2-methylindole-3-ylglyoxyloyl)-4-nitrosopiperazine. Purification is accomplished by recrystallization from DMF and water to produce crystals having a m.p. 231°–232° C. Analysis: Calculated for $C_{15}H_{15}N_4O_3$:59.99% C; 5.04% H; 18.66% N Found:60.36% C; 5.28% H; 18.76% N.

b. To a stirred mixture of 9.0 g of lithium aluminum hydride in 400 ml. of 1,2-dimethoxyethane is added 10.52 g (0.35 mol) of 1-(2-methylindol-3-ylglyoxyloyl)-4-nitrosopiperazine slowly to maintain reaction temperature below 35° C. After all the material is added, the mixture is refluxed for 14–16 hours. The reaction mixture is cooled to −5° C. and a solution of 50 ml. of water and 50 ml. of 1,2-dimethoxyethane is slowly added while maintaining the temperature below 15° C. Another 50 ml. of water is added. The mixture is then filtered, the solvent is removed, and the residual solid is recrystallized from hot benzene, producing the pure crystals of 3-[2-(4-aminopiperazin-1-yl)ethyl]-2-methylindole, m.p. 118°–120° C. Analysis: Calculated for $C_{15}H_{22}N_4$: 71.08% C; 8.21% H; 20.72% N Found:71.11% C; 8.28% H; 20.75% N.

EXAMPLE 3

3-(4-Aminopiperazin-1-yl) methylindole a. A mixture of 34.8 g (0.22 mol) of gramine and 23.9 g (0.20 mol) of nitrosopiperazine in 700 ml. of toluene is refluxed while stirring under nitrogen for 48 hours. The reaction solution is then concentrated under reduced pressure until a precipitate appears and then is cooled to 0° C. and is filtered. The product is washed with cold toluene and dried to produce crystals of 3-(4-nitrosopiperazin-1-yl)methylindole. This product is recrystallized from toluene to yield pure plates, m.p. 116°–118° C. Analysis: Calculated for $C_{13}H_{16}N_4O$: 63.92% C; 6.60% H; 22.93% N Found: 63.84% C; 6.64% H; 23.06% N.

b. To a stirred mixture of 10.5 g of lithium aluminum hydride in 100 ml. of 1,2-dimethoxyethane is added slowly 38 g (0.16 mol) of 3-(4-nitrosopiperazin-1-yl) methylindole while maintaining the temperature below 35° C. After total addition of the material, the mixture is refluxed for four hours. The reaction mixture is cooled to 0° C. and a solution of 50 ml. of water and 50 ml. of 1,2-dimethoxyethane is added slowly maintaining the temperature below 20° C. and an additional 50 ml. of water is added. The mixture is filtered and the solvent is removed from the filtrate. The residual solid is recrystallized from ethanol and water (2:1) to produce pure flakes of 3-(4-aminopiperazin-1-yl) methylindole, m.p. 147°–149° C. Analysis: Calculated for $C_{13}H_{18}N_4$:67.80% C; 7.88% H; 24.33% N Found: 67.69% C; 7.94% H; 24.28% N.

EXAMPLE 4

3-[2-(4-Benzamidopiperazin-1-yl)ethyl]indole

A stirred solution of 6.13 g (0.025 mol) of 3-[2-(4-aminopiperazin-1-yl)ethyl]indole as obtained in Example 1, and 3.54 g (0.035 mol) of triethylamine in 75 ml. of chloroform is cooled to 0° C. with exclusion of moisture. A solution of 4.20 g (0.03 mol) of benzoyl chloride in 5 ml. of chloroform is added slowly for 30 minutes, while maintaining the temperature at 0°–5° C. The product starts crystallizing after half the material is added; after total addition, the mixture is stirred for two hours at ambient temperature. Crystalline form is improved by the addition of 75 ml. of 10% sodium hydroxide and 100 ml. of ethyl ether and stirring for an additional 15 minutes. The product is filtered, washed with water, then ethyl ether and dried. This product is recrystallized twice from methanol, then from DMF and water to give powdery crystals of 3-[2-(4-benzamidopiperazin-1-yl)ethyl]indole m.p. 227°–229° C., as the monohydrate. Analysis: Calculated for $C_{21}H_{24}N_4O.H_2O$: 68.83% C; 6.60H; 15.29% N Found: 69.30% C; 6.67% H; 15.31% N.

EXAMPLE 5–23

By following the manipulative procedure described in Example 4, substituting for the benzoyl chloride, the appropriate mono, di or tri substituted benzoyl halide there are produced the 3-[2-(4-substituted-benzamidopiperazin-1-yl)ethyl]indoles, listed in Table III.

Table III

| | | | | | ANALYSIS | | | | | |
|---|---|---|---|---|---|---|---|---|---|---|
| | | | | | Calc'd. | | | Found | | |
| Ex | Substituents | Recryst'n Solvent | Empirical Formula | M.P.° C | %C | %H | %N | %C | %H | %N |
| 5 | p-Methyl | EtOH/$H_2O$ | $C_{22}H_{26}N_4O$ | 231–234 | 72.90 | 7.23 | 15.46 | 72.69 | 7.22 | 15.51 |
| 6 | o-Methyl | MeOH | $C_{22}H_{26}N_4O$ | 211–213 | 72.90 | 7.23 | 15.46 | 73.08 | 7.38 | 15.55 |
| 7 | m-Methyl | DMF/$H_2O$ | $C_{22}H_{26}N_4O$ | 201–203 | 72.90 | 7.23 | 15.46 | 72.79 | 7.46 | 15.37 |
| 8 | p-Methoxy | DMF/$H_2O$ | $C_{22}H_{26}N_4O_2$ | 210–215 dec. | 69.82 | 6.92 | 14.80 | 69.54 | 6.86 | 14.79 |
| 9 | o-Methoxy | MeOH | $C_{22}H_{26}N_4O_2$ | 230–232 | 69.82 | 6.92 | 14.80 | 69.62 | 7.06 | 14.73 |
| 10 | m-Methoxy | DMF/$H_2O$ | $C_{22}H_{26}N_4O_2$ | 220–222 | 69.82 | 6.92 | 14.80 | 69.80 | 6.96 | 14.75 |
| 11 | p-Ethoxy | EtOH/$H_2O$ | $C_{23}H_{28}N_4O_2$ | 202–204 | 70.38 | 7.19 | 14.27 | 70.76 | 7.10 | 14.08 |
| 12 | p-Butoxy | EtOH/$H_2O$ | $C_{25}H_{32}N_4O_2$ | 200–202 | 71.40 | 7.67 | 13.32 | 71.61 | 7.62 | 13.46 |
| 13 | [3,5-Dimethoxy] | EtOAc | $C_{23}H_{28}N_4O_3$ | 195–197 | 67.63 | 6.91 | 13.72 | 67.61 | 6.85 | 13.56 |
| 14 | [3-Methoxy-4-Methyl] | $CH_3CN$ | $C_{23}H_{28}N_4O_2$ | 222–225 | 70.38 | 7.19 | 14.27 | 69.98 | 7.03 | 14.50 |
| 15 | [3,4,5-Trimethoxy] | EtOH/$H_2O$ | $C_{24}H_{30}N_4O_4$ | 161–163 | 65.73 | 6.90 | 12.78 | 65.51 | 6.90 | 12.82 |
| 16 | p-tert-Butyl | EtOH/$H_2O$ | $C_{25}H_{32}N_4O$ | 209–212 | 74.22 | 7.97 | 13.85 | 74.06 | 7.80 | 13.77 |
| 17 | m-Trifluoromethyl | DMF/$H_2O$ | $C_{22}H_{23}F_3N_4O$ | 194–196 | 63.45 | 5.57 | 13.45 | 62.77 | 5.54 | 13.30 |

Table III-continued

| Ex | Substituents | Recryst'n Solvent | Empirical Formula | M.P.° C | Calc'd. %C | %H | %N | Found %C | %H | %N |
|---|---|---|---|---|---|---|---|---|---|---|
| 18 | p-Trifluoromethyl | EtOH/H$_2$O | C$_{22}$H$_{23}$F$_3$N$_4$O | 216–219 | 63.45 | 5.57 | 13.45 | 63.25 | 5.57 | 13.48 |
| 19 | p-Chloro | DMF/H$_2$O | C$_{21}$H$_{23}$ClN$_4$O | 256–259 dec. | 65.88 | 6.05 | 14.63 | 66.13 | 5.95 | 14.85 |
| 20 | p-Fluoro | DMF/H$_2$O | C$_{21}$H$_{23}$FN$_4$O | 256–259 dec. | 68.83 | 6.33 | 15.29 | 68.90 | 6.31 | 15.44 |
| 21 | o-Fluoro | DMF/H$_2$O | C$_{21}$H$_{23}$FN$_4$O | 185–187 | 68.83 | 6.33 | 15.29 | 68.66 | 6.48 | 15.43 |
| 22 | p-Nitro | EtOH/H$_2$O | C$_{21}$H$_{23}$N$_5$O$_3$ | 205–208 | 64.11 | 5.89 | 17.80 | 64.43 | 5.85 | 17.65 |
| 23 | 4-Chloro-3-Sulfamyl | EtOH/H$_2$O | C$_{21}$H$_{24}$ClN$_5$O$_3$S | 135–138 | 54.60 | 5.24 | 15.16 | 54.87 | 5.06 | 15.02 |

EXAMPLE 24

3-[2-(4-p-Hydroxybenzamidopiperazin-1-yl)ethyl]indole

To a stirred mixture of 2.5 g (0.0066 mol) of 3-[2-(4-p-methoxybenzamidopiperazin-1-yl)ethyl]indole, Example 8, in 25 ml of dry 2,4,6-collidine is added 5.0 g of LiI (exothermic t 30° C). The mixture is heated to reflux under nitrogen for 4 hours. The reaction is cooled, acidified with 3N HCl, stirred for 30 minutes and then carefully made basic with sodium carbonate. The oily collidine is extracted with ether and the aqueous layer stripped off in an evaporator. The solid product is triturated with water, filtered, and washed well with water. This material is then dissolved in 10 ml of methanol, absorbed onto a column of 500 g of silica gel made up in benzene, and chromatographed. The fractions eluted with 2% methanol in chloroform are combined and the solvent removed leaving a solid. The solid is recrystallized from an ethanolwater mixture to give a pure product, m.p. 190°–192° C, of 3-[2-(4-p-hydroxybenzamidopiperazin-1-yl)ethyl]indole. Analysis: Calculated for C$_{21}$H$_{24}$N$_4$O$_2$: 69.24% C; 6.59% H; 15.37% N Found: 69.41% C; 6.42% H; 15.14% N.

EXAMPLE 25

3-[2-(4-Biphenylcarbonylamidopiperazin-1-yl)ethyl]indole

A stirred solution of 6.13 g (0.025 mol) of 3-[2-(4-aminopiperazin-1-yl)ethyl]indole obtained according to Example 1, and 3.54 g (0.035 mol) of triethylamine in 100 ml. of chloroform is cooled to −5° C. Then 6.25 g (0.03 mol) of biphenylcarbonyl chloride is added portionwise for 15 minutes maintaining the reaction temperature at 0°–5° C. After total addition, the reaction mixture is stirred at ambient temperature for 3 hours. Then 50 ml. of 10% sodium hydroxide followed by 100 ml. of ethyl ether is added to promote crystallization. The product is filtered, washed well with water and dried. This is recrystallized twice from ethanol and water to give pure white flakes of 3-[2-(4-biphenyl-carbonylamidopiperazin-1-yl)ethyl]indole, m.p. 230°–233° C. Analysis: Calculated for C$_{27}$H$_{28}$N$_4$O: 76.39% C; 6.65% H; 13.20% N Found 76.47% C; 6.66% H; 13.01% N.

EXAMPLES 26–30

By following the manipulative procedure described in Example 25, substituting for the biphenyl carbonyl chloride the appropriate carbonyl chloride, novel compounds listed in Table IV are produced.

TABLE IV

| Ex | R$_4$ | Recryst'n Solvent | Empirical Formula | M.P.° C. | Calculated %C | %H | %N | Found %C | %H | %N |
|---|---|---|---|---|---|---|---|---|---|---|
| 26 | Cyclohexanecarbonyl | EtOH/H$_2$O | C$_{21}$H$_{29}$N$_4$O | 205–208 | 71.15 | 8.53 | 15.80 | 70.94 | 8.57 | 16.03 |
| 27 | 2-Furoyl | EtOH/H$_2$O | C$_{19}$H$_{22}$N$_4$O$_2$ | 201–203 | 67.44 | 6.55 | 16.56 | 67.22 | 6.57 | 16.49 |
| 28α | Norbornanecarbonyl | EtOH/H$_2$O | C$_{22}$H$_{30}$N$_4$O | 178–181 | 72.10 | 8.25 | 15.29 | 71.94 | 8.59 | 15.09 |
| 29 | Adamantanecarbonyl | EtOH/H$_2$O | C$_{25}$H$_{34}$N$_4$O | 214–216 | 73.86 | 8.43 | 13.78 | 73.62 | 8.13 | 13.40 |
| 30 | Diphenylacetyl | EtOH/H$_2$O | C$_{28}$H$_{30}$N$_4$O | 162–163 | 76.58 | 7.11 | 12.75 | 76.46 | 6.94 | 12.85 |

α-Hexane is used to promote crystallization, instead of ether.

EXAMPLE 31

3-[2-(4-Isonicotinoylamidopiperazin-1-yl)ethyl]indole

A stirred solution of 6.13 g (0.025 mol) of 3-(4-aminopiperazin-1-yl)ethyl indole, Example 1, and 3.54 g (0.035 mol) of triethylamine in 100 ml. of chloroform is cooled to 0° C., with exclusion of moisture. Then 5.35 g (0.03 mol) of isonicotinoyl chloride is added portionwise for 15 minutes maintaining the reaction temperature at 0°–5° C. After total addition, the reaction mixture is stirred for 24 hours at ambient temperature. Then 50 ml. of 10% sodium hydroxide is added while stirring. The chloroform layer is separated, washed with water and dried. The solvent is evaporated and the residual solid is recrystallized twice from ethanol and water to give the pure product, 3-[2-(4-isonicotinoylamidopiperazin-1-yl)ethyl]indole, m.p. 227°–229° C. Analysis: Calculated for C$_{20}$H$_{24}$N$_5$O: 68.75% C; 6.63% H; 20.04% N. Found: 68.72% C; 6.72% H; 20.02% N.

In addition, by following the manipulative procedure described in Example 31 above, substituting for isonicotinoyl chloride, nicotinoyl chloride, 4-methyl-2-furoyl chloride, and 2-pyrrolyl chloride, the following novel compounds are obtained:

3-[2-(4-nicotinoylamidopiperazin-1-yl)ethyl]indole;
3- 2-[4-(4-methyl-2-furoylamido)piperazin-1-yl]ethyl indole; and 3- 2-[4-(2-pyrroylamido)piperazin-1-yl]ethyl indole; respectively.

EXAMPLE 32

3-[2-(4-p-Isopropylbenzamidopiperazin-1-yl)ethyl]indole hydrochloride a. p-isopropylbenzaldehyde is oxidized to the corresponding benzoic acid by using potassium permanganate in sulfuric acid as the oxidizing agent at low temperature. The acid is converted to the acid chloride using thionyl chloride with a trace of dimethylformamide as a catalyst to give p-isopropylbenzoyl chloride.

b. A stirred solution of 6.13 g (0.025 mol) of 3-[2-(4-aminopiperazin-1-yl)ethyl]indole obtained according to Example 1, and 3.54 g (0.035 mol) of triethylamine in 75 ml. of chloroform is cooled to 0° C., with exclusion of moisture. A solution of 5.57 g (0.03 mol) of p-isopropylbenzoyl chloride in 5 ml. of chloroform is added dropwise over a 30 minute span, while maintaining a reaction temperature of 0°–5° C. After total addition, the mixture is stirred at ambient temperature for two hours. Then 50 ml. of 10% sodium hydroxide is added to the reaction and stirring is continued for 30 minutes. The chloroform layer is separated and concentrated under reduced pressure. The residual solid is converted to the hydrochloride salt by dissolving it in ethanol and adding an equal volume of hydrogen chloride in ether. The precipitated salt is recrystallized from isopropanol and ether to yield 3-[2-(4-p-isopropylbenzamidopiperazin-1-yl)ethyl]indole hydrochloride, m.p. 209°–210° C. Analysis: Calculated for $C_{24}H_{30}NO\cdot HCl$: 67.51% C; 7.32% H; 13.12% N; 8.54% Cl Found: 67.78% C; 7.30% H; 13.04% N; 8.49% CL.

EXAMPLE 33

3-[1-Hydroxy-2-(4-benzamidopiperazin-1-yl)ethyl]indole a. To a stirred mixture of 9.0 g of lithium aluminum hydride in 400 ml. of tetrahydrofuran is added 10.5 g. (0.037 mol.) of 1-(indol-3-ylglyoxyloyl)-4-nitrosopiperazine, obtained according to Example 1 (a), while maintaining the reaction temperature below 35° C. After total addition of the material, the mixture is refluxed for 14–16 hours. In this lower boiling solvent, the reduction is incomplete and 3-[1-hydroxy-2-(4-aminopiperazin-1-yl)ethyl]indole and 3-[2-(4-aminopiperazin-1-yl)ethyl] indole are produced. The partially reduced product is separated from the totally reduced material by crystallization from ethanol to give pure crystals of 3-[1-hydroxy-2-(4-aminopiperazin-1-yl) ethyl]indole, m.p. 174°–177° C. Analysis: Calculated for $C_{14}H_{20}N_4O$: 64.59% C 7.74% H; 21.52% N Found: 64.54% C; 7.84% H; 21.80% N.

b. To a stirred slurry of 8.60 g (0.0334 mol) of 3-[1-hydroxy-2-(4aminopiperazin-1-yl)ethyl]indole in 50 ml. of chloroform is added 4.55 g (0.045 mol) of triethylamine. The mixture is cooled to 0° C. under a nitrogen atmosphere, and a solution of 5.64 g (0.040 mol) benzoyl chloride in 10 ml. of chloroform is introduced dropwise for 1 hour, while maintaining the reaction temperature of 0°–5° C. The resulting mixture is stirred at 0° C. for one hour, and at ambient temperature for another hour. The mixture is diluted with 150 ml. of chloroform and then 100 ml. of 10% sodium hydroxide. This mixture is stirred for 15 minutes and then filtered; the cake is washed well with water and dried to give a white solid. This product is recrystallized first from an ethanol and water mixture and then twice from DMF and water to give pure white crystals of 3-[1-hydroxy-2-(4-benzamidopiperazin-1-yl)ethyl]indole, m.p. 211°–213° C. dec. Analysis: Calculated for $C_{21}H_{24}N_4O_2$: 69.21% C; 6.64% H; 15.37% N Found: 69.00% C; 6.60% H; 15.28% N.

EXAMPLE 34

3-[2-(4-Acetamidopiperazin-1-yl)ethyl]indole

A stirred solution of 7.34 g (0.03 mol) of 3-[2-(4-aminopiperazin-1-yl)ethyl]indole obtained according to Example 1, and 6.12 g (0.06 mol) of acetic anhydride in 75 ml. of benzene is heated to 50° C. and is allowed to react for 2 hours; a fine white precipitate appears. The reaction mixture is then stirred at ambient temperature for two more hours. The product is filtered, washed with ethyl ether, and dried. The product is thereafter crystallized from an ethanol and water mixture (1:1) to give white crystals of 3-[2-(4-acetamidopiperazin-1-yl)ethyl]indole, m.p. 183°–186° C. Analysis: Calculated for $C_{16}H_{22}N_4O$: 67.11% C; 7.74% H; 19.56% N Found: 67.14% C; 7.85% H; 19.76% N.

EXAMPLE 35

3-[2-(4-Benzamidopiperazin-1-yl)ethyl]-2-methylindole

A stirred solution of 7.70 g (0.03 mol) of 3-[2-(4-aminopiperazin-1-yl)ethyl]-2-methylindole obtained according to Example 2, and 3.54 g (0.035 mol) of triethylamine in 75 ml. of chloroform is cooled to −5° with exclusion of moisture. Then a solution of 4.20 g (0.03 mol) of benzoyl chloride in 5 ml. of chloroform is added slowly for a half hour, maintaining the reaction temperature at 0°–5° C. After total addition, the solution is stirred for two hours at ambient temperature. Then 50 ml. of sodium hydroxide followed by 50 ml. of ethyl ether is added to promote crystallization. After thirty minutes an additional 75 ml. of ethyl ether is introduced to improve the crystalline form. The product is filtered, washed with water, then ethyl ether and dried. The product is recrystallized twice from a DMF and water mixture to give white crystals of 3-[2-(4-benzamidopiperazin-1-yl)ethyl]-2-methylindole, m.p. 130°–133° C. Analysis: Calculated for $C_{22}H_{26}N_4O$: 72.90% C; 7.23% H; 15.46% N Found: 72.91% C; 7.51% H; 15.82% N.

EXAMPLE 36 AND 37

By following the manipulative procedure described in Example 35, but substituting for benzoyl chloride the appropriate substituted benzoyl chloride, the 3-[2-(4-substituentbenzamidopiperazin-1-yl)ethyl]-2-methylindole listed in Table V is produced. In these two examples, the crude crystalline product is not washed initially with water, it is only washed with ethyl ether.

Table V

| | | | | | | Analysis | | | | |
|---|---|---|---|---|---|---|---|---|---|---|
| | | Recryst'n | Empirical | | | Calc'd. | | | Found | |
| Ex | Substituent | Solvent | Formula | M.P.° C. | %C | %H | %N | %C | %H | %N |
| 36 | p-Fluoro | DMF/H$_2$O | C$_{22}$H$_{25}$FN$_4$O | 222–224 | 69.45 | 6.62 | 14.73 | 69.69 | 6.74 | 15.01 |

Table V-continued

| Ex | Substituent | Recryst'n Solvent | Empirical Formula | M.P.° C. | %C | Calc'd. %H | %N | Found %C | %H | %N |
|---|---|---|---|---|---|---|---|---|---|---|
| 37 | p-Nitro | EtOH/H$_2$O | C$_{22}$H$_{25}$N$_5$O$_3$ | 136–139 | 64.85 | 6.18 | 17.19 | 64.58 | 6.03 | 17.07 |

EXAMPLE 38

3-[2-(4-Benzamidopiperazin-1-yl)ethyl]-5,6-dimethoxy- 2-methylindole a. A stirred mixture of 3.82 g (0.02 mol) of 5,6-dimethoxy-2-methylindole and 5,80 g (0.044 mol) of potassium carbonate in 50 ml. of chloroform and 15 ml. of water is cooled to −5° C. Then 3.2 g (0.024 mol) of oxalyl chloride is added slowly, maintaining the reaction temperature at 0° C. The resulting mixture is stirred at room temperature for 10 minutes. Then 3.5 g (0.03 mol) of nitrosopiperazine is added over a 5 minute span. The reaction mixture turns red-purple and is stirred for an additional hour. To the solution is slowly added in portions 250 ml. of ethyl ether; the solution appears lighter and a tan precipitate forms. After stirring for one hour, the product is filtered, washed well with water and dried. This product is recrystallized from a DMF and water mixture to give flakes of 1-(5,6-dimethoxy-2-methylindol-3-ylglyoxyloyl)-4-nitrosopiperazine, m.p. 233°–225° C. Analysis: Calculated for C$_{17}$H$_{20}$N$_4$O$_5$: 56.66% C; 5.59% H; 15.55% N Found: 56.65% C; 5.61% H; 15.68% N.

b. To a stirred mixture of 9.0 g of lithium aluminium hydride in 400 ml. of 1,2-dimethoxyethane is slowly added 11 g of 1-(5,6-dimethoxy-2-methylindol-3-ylglyoxyloyl)-4-nitrosopiperazine while maintaining the temperature below 35° C. After total addition, the mixture is refluxed for 14–16 hours. The reaction mixture is then cooled to −5° C. and a solution of 50 ml. of water and 50 ml. of 1,2-dimethoxyethane is slowly added keeping the temperature below 15° C., followed by an additional 50 ml. of water. Upon filtration and removal of the solvent and amorphous foam of 3-[2-(4-aminopiperazin-1-yl) ethyl]5,6-dimethoxy-2-methylindole is obtained, which could not be solidified by crystallization or salt formation. Infrared (IR) and nuclear magnetic resonance (NMR) analysis confirms the aforementioned structure.

c. A stirred mixture of 7.92 g (0.025 mol) of 3-[2-(4-aminopiperazin-1-yl)ethyl]-5,6-dimethoxy-2-methylindole and 3.54 g (0.035 mol) of triethylamine in 75 ml. of chloroform is cooled to −5° C., with the exclusion of moisture. Then a solution of 4.20 g (0.03 mol) of benzoyl chloride in 6 ml. of chloroform is added dropwise over a 30 minute span, while maintaining a temperature of 0°–5° C. After total addition, the mixture is stirred at ambient temperature for two hours. Then 50 ml. of 10% sodium hydroxide is added, followed by 50 ml. of ethyl ether to promote crystallization. After stirring for 15minutes, another 100 ml. of ethyl ether is added to improve crystallization form. The product is filtered, washed well with water, then ethyl ether and dried. This crystalline product is recrystallized twice from DMF and water mixture to give pure needles of 3-[2-(4-benzamidopiperazin-1-yl)ethyl]-5,6-dimethoxy-2-methylindole, m.p. 128°–131° C. Analysis: Calculated for C$_{24}$H$_{30}$N$_4$O$_3$: 68.22% C; 7.16% H; 13.26% N Found: 68.03% C; 7.14% H; 13.12% N.

EXAMPLE 39

5,6-Dimethoxy-3-[2-(4-p-fluorobenzamidopiperazin-1-yl)ethyl]-2-methylindole

A stirred solution of 7.92 g (0.025 mol) of 3-[2-(4-aminopiperazin-1-yl)ethyl]-5,6-dimethoxy-2-methylindole, obtained according to Example 38 (b), and 3.54 g (0.035 mol) of triethylamine in 75 ml. of chloroform is cooled to −5° C. with exclusion of moisture. A solution of 4.75 g (0.03 mol) of p-fluorobenzoyl chloride in 5 ml. of chloroform is slowly added over a 30 minute span, while maintaining the reaction temperature at 0°–5° C. After total addition, the mixture is stirred for two hours at ambient temperature. Then 50 ml. of 10% sodium hydroxide followed by 50 ml. of ethyl ether is added to promote crystallization. The mixture is stirred for 30 minutes and an additional 75 ml. of ethyl ether is added to improve the crystalline form. The product is filtered, washed with water, ethyl ether, and then dried. The product is recrystallized twice from an ethanol and water mixture to give white crystals of 5,6-dimethoxy-3-[2-(4-p-fluorobenzamidopiperazin-1-yl)ethyl]-2-methylindole, m.p. 116°–119° C. Analysis: Calculated for C$_{24}$H$_{29}$FN$_4$O$_3$: 64.43% C; 6.64% H; 12.71% N Found: 64.29% C; 6.59% H; 12.50% N.

EXAMPLE 40

5,6-Dimethoxy-3-[2-(4-o-methoxybenzamidopiperazin-1-yl)ethyl]-2-methylindole Hydrochloride A stirred solution of 7.92 g (0.025 mol) of 3-[2-(4-aminopiperazin-1-yl)ethyl]-5,6-dimethoxy-2-methylindole, obtained according to Example 38 (b), and 3.54 g (0.035 mol) of triethylamine in 75 ml. of chloroform is cooled to 0° C. with exclusion of moisture. Then 5.12 g (0.03 mol) of o-anisoyl chloride dissolved in 5 ml. of chloroform is added dropwise for a 30 minute span while maintaining the reaction temperature at 0°–5° C. After total addition, the solution is stirred at ambient temperature for 3 hours. Then 50 ml. of 10% sodium hydroxide is added and the mixture is stirred for 15 minutes. The chloroform layer is separated, and concentrated until a residue remains.

The above residue is dissolved in ethanol, a solution of hydrogen chloride in ethyl ether is introduced until the turbidity point is attained, and then ether is added with vigorous stirring. The product is filtered and washed well with ethyl ether. This product is recrystallized from isopropanol to give a white crystalline powder of 5,6-dimethoxy-3-[2-(4-o-methoxybenzamidopiperazin-1-yl)ethyl]-2-methylindole hydrochloride, m.p. 122°–123° C., dec. Analysis: Calculated for C$_{25}$H$_{22}$N$_4$O$_4$.HCl: 62.69% C; 4.84% H; 11.69% N; 7.40% Cl Found: 62.40% C; 4.60% H; 11.64% N; 7.38% Cl.

EXAMPLE 41

5,6-Dimethoxy-2-methyl-3-[2-(4-p-trifluoromethyl-benzamidopiperazin-1-yl)ethyl]indole Hydrochloride By following the manipulative procedure in Example 40, substituting for the o-anisoyl chloride as the acylating agent, p-trifluoromethylbenzoyl chloride, the pure product of 5,6-demethoxy-2-methyl-3-[2-(4-p-trifluoromethylbenzamidopiperazin-1-yl)ethyl]indole hydrochloride, m.p. 172°–175° C. is formed. Analysis:- Calculated for $C_{25}H_{29}F_3N_4O \cdot HCl$: 60.66% C; 6.11% H; 11.32% N; 7.16% Cl; 11.52% F Found:60.32% C; 6.09% H; 11.38% N; 7.19% Cl; 11.55% F.

EXAMPLE 42

3-(4-Benzamidopiperazin-1-yl) methylindole

A stirred solution of 6.9 g (0.03 mol) of 3-(4-aminopiperazin-1-yl)methylindole obtained according to Example 3, and 4.05 g (0.04 mol) of triethylamine in 75 ml. of chloroform is cooled to −5° C., with exclusion of moisture. A solution of 4.35 g (0.035 mol) of benzoyl chloride in 5 ml. of chloroform is added dropwise over a fifteen minute span while maintaining a reaction temperature of 0°–5° C. After total addition, the mixture is stirred at ambient temperature for 2 hours. Then 50 ml. of 10% sodium hydroxide solution is added, followed by Found: ml. of ethyl ether to promote crystallization. The reaction mixture is stirred for another 30 minutes and an additional 50 ml. of ether is added to improve the crystalline form. The product is filtered, washed well with water, then ethyl ether, and dried. This product is recrystallized twice from an ethanol and water mixture to give pure white flakes of 3-(4-benzamidopiperazin-1-yl) methylindole, m.p. 176°–178° C. Analysis:Calculated for $C_{20}H_{21}N_4O$:71.83% C; 6.63% H; 16.75% N Found:72.10% C; 6.53% H; 16.71% N.

EXAMPLES 43 and 44

By following the manipulative procedure described in Example 42, wherein the acylation agent is the appropriate substituted benzoyl chloride, the 3-[4-($R_4$-benzamido)piperazin-1yl]methylindole listed in Table VI is produced.

TABLE VI

| Ex | $R_4$ Substituent | Recryst'n Solvent | Empirical Formula | M.P.° C. | %C | Calc'd. %H | %N | Found %C | %H | %N |
|----|---|---|---|---|---|---|---|---|---|---|
| 43 | 3,4,5-Trimethoxy | EtOH/H$_2$O | $C_{23}H_{28}N_4O_4$ | 206–208 | 65.08 | 6.65 | 13.20 | 65.15 | 6.45 | 10.00 |
| 44 | p-Fluoro | EtOH/H$_2$O | $C_{20}H_{21}N_4FO$ | 206–208 | 68.16 | 6.01 | 15.89 | 68.15 | 6.03 | 15.79 |

EXAMPLES 45-47

By following the manipulative procedure described in Example 31, substituting for isomcotinoyl chloride the appropriate carbonyl chloride, novel compounds listed in Table VII are produced.

TABLE VII

| Ex | $R_4$ Substituent | Recryst'n Solvent | Empirical Formula | M.P.°C. | %C | Calc'd. %H | %N | Found %C | %H | %N |
|----|---|---|---|---|---|---|---|---|---|---|
| 45 | 5-bromo-2-furoyl | EtOH/H$_2$O | $C_{19}H_{21}BrN_4O_2$ | 195–198 | 54.69 | 5.07 | 13.42 | 54.76 | 5.21 | 13.08 |
| 46 | pyrazinoyl | Isopropanol | $C_{19}H_{23}N_6O$ | 195–197 | 64.97 | 6.54 | 23.91 | 64.88 | 6.44 | 23.68 |
| 47 | 2-thienyl | EtOH/H$_2$O | $C_{18}H_{22}N_4OS$ | 139–141 | 64.37 | 6.25 | 15.51 | 64.03 | 6.34 | 15.43 |

We claim:

1. A compound selected from the group depicted by the formulae:

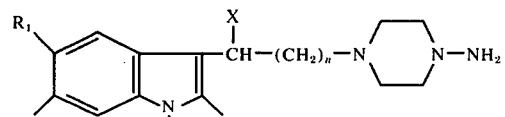

and

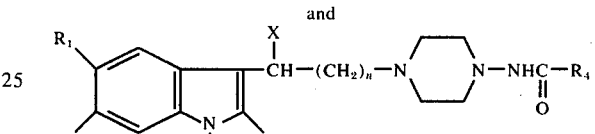

wherein X is a member selected from the group consisting of hydrogen and hydroxy; n is 0 or 1; $R_1$ and $R_2$ each is a member selected from the group consisting of hydrogen and alkoxy of 1–2 carbon atoms; $R_3$ is a member selected from the group consisting of hydrogen and alkyl of 1–3 carbon atoms; and $R_4$ is a member selected from the group consisting of alkyl of 1–4 carbon atoms, benzhydryl, cycloalkyl of 6 to 10 carbon atoms, bridged cycloalkyl of 6–10 carbon atoms, phenyl; mono, di, and tri substituted phenyl, wherein the substituents are selected from the group consisting of alkyl of 1 to 4 carbon atoms, alkoxy of 1 to 4 carbon atoms, halogen, trifluoromethyl, phenyl, sulfamyl, nitro and hydroxy; furyl; substituted furyl wherein the substituents are selected from the group consisting of halogen and lower alkyl; thienyl; pyrroyl; pyrazinyl; pyridyl; and a physiologically tolerable acid addition salt thereof.

2. A compound as defined in claim 1 and wherein X is a member selected from the group consisting of hydrogen and hydroxy, n is 0 or 1, and $R_3$ is methyl.

3. A compound as defined in claim 1 and wherein X is hydrogen, n is 1, $R_1$ and $R_2$ each is a member selected from the group consisting of hydrogen and methoxy; $R_3$ is a member of the group consisting of a hydrogen atom and methyl; $R_4$ is a member of the group consisting of a methyl, benzhydryl, cyclohexyl, norbornyl, adamantyl, isonicotinyl, furyl, mono substituted furyl wherein the substituents are bromo or methyl, phenyl, mono, di or tri substituted phenyl wherein the substituents are alkyl of 1 to 4 carbon atoms, alkoxy of 1 to 4 carbon atoms, chlorine, fluorine, trifluoromethyl, phenyl, sulfamyl or nitro; thienyl, pyrroyl, pyrazinyl and a physiologically tolerable acid addition salt thereof.

4. The compound as defined in claim 1 and wherein $R_1$ and $R_2$ is hydrogen, $R_3$ is hydrogen or methyl, n is 1, X is hydrogen and $R_4$ is furyl or a substituted furyl, wherein the substituents are bromo or methyl.

5. The compound as defined in claim 1 and wherein the same is 3-[2-(4-aminopiperazin-1-yl)ethyl]indole or a physiologically tolerable acid addition salt thereof.

6. The compound as defined in claim 1 and wherein the same is 3-(4-aminopiperazin-1-yl)methylindole or a physiologically tolerable acid addition salt thereof.

7. The compound as defined in claim 1 and wherein the same is 3-[1-hydroxy-2-(4-aminopiperazin-1-yl) ethyl]indole or a physiologically tolerable acid addition salt thereof.

8. The compound as defined in claim 1 and wherein the same is 3-[2-(4-aminopiperazin-1-yl)ethyl]-5,6-dimethoxy-2-methylindole or a physiologically tolerable acid addition salt thereof.

9. The compound as defined in claim 1 and wherein the same is 3-[2-(4-benzamidopiperazin-1-yl)ethyl]indole and a physiologically tolerable acid addition salt thereof.

10. The compound as defined in claim 1 and wherein the same is 3-[1-hydroxy-2-(4-benzamidopiperazin-1-yl)ethyl] indole and a physiologically tolerable acid addition salt thereof.

11. The compound as defined in claim 1 and wherein the same is 3-[2-(4-acetamidopiperazin-1yl)ethyl]indole and a physiologically tolerable acid addition salt thereof.

12. The compound as defined in claim 1 and wherein the same is 3-{2-[4-(2-furoylamido)piperazin-1-yl]ethyl}indole and a physiologically tolerable acid addition salt thereof.

13. The compound as defined in claim 1 and wherein the same is 3-{2-[4-(5-bromo-2-furoylamido)piperazin-1-yl]ethyl}indole, and a physiologically tolerable acid addition salt thereof.

14. The compound as defined in claim 1 and wherein the same is 3-{2-[4-(4-methyl-2-furoylamido)piperazin-1-yl]ethyl } indole and a physiologically tolerable acid addition salt thereof.

15. The compound as defined in claim 1 and wherein the same is 3-[2-(4-norbornanecarbonylamidopiperazin-1yl)ethyl]indole and a physiologically tolerable acid addition salt thereof.

16. The compound as defined in claim 1 and wherein the same is 3-[2-(4-benzamidopiperazin-1-yl)ethyl]-2-methylindole and a physiologically tolerable acid addition salt thereof.

17. The compound defined in claim 1 and wherein the same is 3-[2-(4-benzamidopiperazin-1-yl)ethyl]-5,6-dimethoxy-2-methylindole and a physiologically tolerable acid addition salt thereof.

18. A compound selected from the group depicted by the formula:

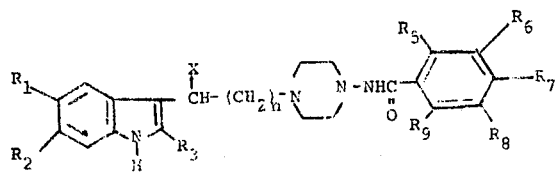

wherein X is a member selected from the group consisting of hydrogen and hydroxy; n is 0 or 1, $R_1$ and $R_2$ each is a member selected from the group consisting of hydrogen and alkoxy of 1-2 carbon atoms; $R_3$ is a member selected from the group consisting of hydrogen and alkyl of 1-3 carbon atoms, wherein $R_5$, $R_6$, $R_7$, $R_8$, and $R_9$ each is a member selected from the group consisting of hydrogen, halogen of molecular weight less than 80, straight or branched chain alkyl of 1-4 carbon atoms, hydroxy, alkoxy of 1-4 carbon atoms, trifluoromethyl, nitro, phenyl and sulfamyl; and the physiologically tolerable acid addition salts thereof.

19. The compound as defined in claim 18 wherein the same is 3-[2-(4-p-fluorobenzamidopiperazin-1-yl)ethyl]indole and a physiologically tolerable acid addition salt thereof.

20. The compound as defined in claim 18 wherein the same is 3-{2-[4-(3,4,5-trimethoxybenzamido)piperazin-1-yl[ethyl } indole and a physiologically tolerable acid addition salt thereof.

21. The compound as defined in claim 18 wherein the same is 3-[2-(4-p-tert-butylbenzamidopiperazin-1-yl)ethyl]indole and a physiologically tolerable acid addition salt thereof.

22. The compound as defined in claim 18 wherein the same is 3-[2-(4-p-trifluoromethylbenzamidopiperazin-1yl)ethyl] indole and a physiologically tolerable acid addition salt thereof.

23. The compound as defined in claim 18 wherein the same is 3-[2-(4-p-isopropylbenzamidopiperazin-1-yl)ethyl] indole and a physiologically tolerable acid addition salt thereof.

24. The compound as defined in claim 18 wherein the same 3-[2-(4-p-fluorobenzamidopiperazin-1-yl)ethyl]-2-methyl indole and a physiologically tolerable acid addition salt thereof.

25. The compound as defined in claim 18 wherein the same is 3-[2-(4-p-hydroxybenzamidopiperazin-1-yl)ethyl]indole and a physiologically tolerable acid addition salt thereof.

26. The compound as defined in claim 18 wherein the same is 3-{2-[4-(3,5-dimethoxybenzamido)piperazin-1-yl]ethyl}indole and a physiologically tolerable acid addition salt thereof.

27. A process for preparing a compound selected from the group depicted by the formula:

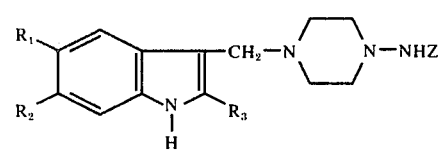

wherein Z is

$R_1$ and $R_2$ each is a member selected from the group consisting of hydrogen and alkoxy of 1 to 2 carbon atoms; $R_3$ is a member selected from the group consisting of hydrogen and alkyl of 1 to 3 carbon atoms; and $R_4$ is a member selected from the group consisting of alkyl of 1 to 4 carbon atoms, benzhydryl, cycloalkyl of 6 to 10 carbon atoms, bridged cycloalkyl of 6 to 10 carbon atoms, phenyl, mono, di, and tri substituted phenyl, wherein the substituents are selected from the group consisting of alkyl of 1 to 4 carbon atoms, alkoxy of 1 to 4 carbon atoms, halogeno, trifluoromethyl, phenyl, sulfamyl, nitro and hyroxy; furyl, substituted furyl wherein the substituents are selected from the group consisting of halogeno and lower alkyl; thienyl; pyrrolyl; pyrazinyl; and pyridyl; which comprises reacting, with N-nitrosopiperazine, an indole of the formula:

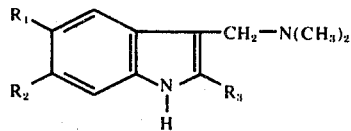

wherein $R_1$, and $R_2$, and $R_3$ are as defined above;
  reducing the resulting intermediate with an alkali metal hydride in an inert solvent and recovering the corresponding 3-(4-aminopiperazin-1-yl) methylindole; and
  acylating the amino moiety on said 3-(4-aminopiperazinyl-1-yl)methylindole with an acid of the formula $R_4COOH$, an acyl halide of the formula $R_4COHal$ wherein the halogen moiety is chloro, bromo, or fluoro, or an acid anhydride of the formula $R_4COOOCR_4$ wherein $R_4$ may be the same or different and is as previously defined.

28. The process according to claim 27, wherein $R_1$, $R_2$, and $R_3$ are hydrogen.

29. The process according to claim 28, wherein the indole is β-dimethyl-amino-methyl indole.

30. The process according to claim 28, wherein the reducing is carried out by lithium aluminum hydride and the inert solvent is 1,2-dimethoxyethane.

31. A process for preparing a compound selected from the group depicted by the formula:

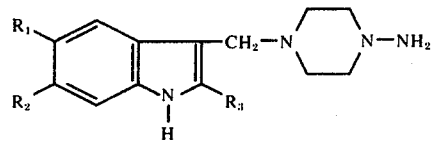

wherein $R_1$ and $R_2$ each is a member selected from the group consisting of hydrogen and alkoxy of 1 to 2 carbon atoms and $R_3$ is a member selected from the group consisting of hydrogen and alkyl of 1 to 3 carbon atoms which comprises reacting, with N-nitrosopiperazine, an indole of the formula

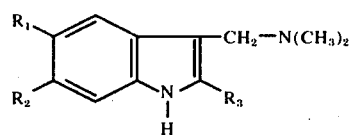

wherein $R_1$, $R_2$, and $R_3$ are as defined above and reducing the resulting intermediate with an alkali metal hydride.

32. The process according to claim 31, wherein the reacting of N-nitrosopiperazine with the indole is carried out with a refluxing toluene solvent.

* * * * *

UNITED STATES PATENT AND TRADEMARK OFFICE
CERTIFICATE OF CORRECTION

PATENT NO. : 3,997,539
DATED : December 14, 1976
INVENTOR(S) : Glamkowski et al.

It is certified that error appears in the above-identified patent and that said Letters Patent are hereby corrected as shown below:

Column 3, line 15, change "...piperazin--yl)..." to --...piperazin-1-yl)...--;

Column 7, line 26, change "3-{2-[3,5-..." to --3-{2-[4-(3,5-...--;

Column 11, line 21, change "t  30°C" to --t→30°C--;

line 46, change "ethanolwater" to --ethanol-water--;

Column 12, lines 66 and 67, change "3- 2-[4-..." to --3-{2-[4-...--;

lines 67 and 68, change "...ethyl indole" to --...ethyl} indole--;

Column 13, line 54, change "...2-(4amino..." to --...2-(4-amino...--;

lines 57 and 58, change "(0.040 mol) benzoyl" to --(0.040 mol) of benzoyl--;

Column 17, line 18, change "5,6-demethoxy..." to --5,6-dimethoxy...--;

line 38, change "by Found: mL of" to --by 50 mL of--;

line 52, change "...piperazin-1yl]..." to --...piperazin-1-yl]...--;

In Table VI, under "Analysis, Found, %N", first number in last column, change "10.00" to --13.10--;

UNITED STATES PATENT AND TRADEMARK OFFICE
CERTIFICATE OF CORRECTION

PATENT NO. : 3,997,539
DATED : December 14, 1976
INVENTOR(S) : Glamkowski et al.

It is certified that error appears in the above-identified patent and that said Letters Patent are hereby corrected as shown below:

Column 18, In Table VII, under "Analysis, Found, %N," first number in last column, change "13.08" to --13.43--;

Claim 3, line 54, delete "a";

Claim 7, line 14, add a hyphen (-) after "...piperazin-1-yl)";

Claim 10, line 27, change "...ethyl] indole" to --...ethyl]indole--;

Claim 15, line 47, change "...-lyl)..." to --...-1-yl)...--;

Claim 20, line 19, change "...-1-yl[ethyl..." to --...-1-yl]ethyl...--;

Claim 22, line 27, change "...-lyl)..." to --...-1-yl)...--;

Claim 23, line 31, change "...ethyl] indole" to --...ethyl]indole--.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks